(12) United States Patent
Nishimura et al.

(10) Patent No.: US 10,143,436 B2
(45) Date of Patent: Dec. 4, 2018

(54) PARTICLE THERAPY SYSTEM

(71) Applicant: HITACHI, LTD., Tokyo (JP)

(72) Inventors: Arao Nishimura, Tokyo (JP); Koji Matsuda, Tokyo (JP); Ryosuke Shinagawa, Tokyo (JP); Taisuke Takayanagi, Tokyo (JP); Masahiro Tadokoro, Tokyo (JP); Takao Kidani, Tokyo (JP); Hideaki Nihongi, Sapporo (JP); Kikuo Umegaki, Sapporo (JP); Taeko Matsuura, Sapporo (JP)

(73) Assignee: Hitachi, Ltd., Tokyo (JP)

( * ) Notice: Subject to any disclaimer, the term of this patent is extended or adjusted under 35 U.S.C. 154(b) by 464 days.

(21) Appl. No.: 14/655,192

(22) PCT Filed: Oct. 10, 2013

(86) PCT No.: PCT/JP2013/077642
§ 371 (c)(1),
(2) Date: Jun. 24, 2015

(87) PCT Pub. No.: WO2014/103471
PCT Pub. Date: Jul. 3, 2014

(65) Prior Publication Data
US 2015/0374324 A1    Dec. 31, 2015

(30) Foreign Application Priority Data

Dec. 25, 2012 (JP) ................................. 2012-280795

(51) Int. Cl.
*A61B 6/00* (2006.01)
*A61N 5/10* (2006.01)

(52) U.S. Cl.
CPC ............ *A61B 6/542* (2013.01); *A61N 5/1049* (2013.01); *A61N 5/1067* (2013.01);
(Continued)

(58) Field of Classification Search
CPC .... A61N 2005/1061; A61N 2005/1087; A61N 5/1049; A61N 2005/1074; A61N 5/1077; A61B 6/5235
See application file for complete search history.

(56) References Cited

U.S. PATENT DOCUMENTS

| 5,813,985 A * | 9/1998 | Carroll ................. A61N 5/1048 600/1 |
| 2003/0016854 A1 | 1/2003 | Inoue et al. |
| 2011/0182411 A1 | 7/2011 | Shinagawa et al. |

FOREIGN PATENT DOCUMENTS

| CN | 1384661 A | 12/2002 |
| EP | 2 324 768 A1 | 5/2011 |

(Continued)

OTHER PUBLICATIONS

Extended European Search received in corresponding European Application No. 13869726.3 dated Jul. 12, 2016.
(Continued)

*Primary Examiner* — Christine H Matthews
(74) *Attorney, Agent, or Firm* — Mattingly & Malur, PC

(57) ABSTRACT

The particle therapy system includes a particle beam generator for generating a particle beam; an irradiation nozzle arranged in a treatment room and irradiating a target with the particle beam; a particle beam transport system communicating the particle beam generator with the irradiation nozzle; an X-ray imaging device arranged in the treatment room and imaging the position of the target through irradiation with X-rays; a dosimeter arranged at a position passed by the particle beam in the irradiation nozzle; and a control apparatus performing control to exclude the measurement result of the X-rays from the measurement result obtained using the dosimeter when the X-rays are emitted during treatment.

20 Claims, 13 Drawing Sheets

(52) U.S. Cl.
CPC ......... *A61N 5/1071* (2013.01); *A61N 5/1075* (2013.01); *A61N 5/1077* (2013.01); *A61N 2005/1061* (2013.01); *A61N 2005/1074* (2013.01); *A61N 2005/1087* (2013.01); *F04C 2270/041* (2013.01)

(56) References Cited

FOREIGN PATENT DOCUMENTS

| | | | |
|---|---|---|---|
| JP | 2011-217902 | A | 11/2011 |
| JP | 2012-506734 | A | 3/2012 |
| WO | 2010/062560 | A2 | 6/2010 |

OTHER PUBLICATIONS

International Search Report of PCT/JP2013/077642.
Chinese Office Action received in corresponding Chinese Application No. 201380068001.3 dated Mar. 9, 2017.
International Preliminary Report on Patentability received in corresponding International Application No. PCT/JP2013/077642 dated Jul. 9, 2015.

\* cited by examiner

PARTICLE THERAPY SYSTEM

TECHNICAL FIELD

The present invention relates to a particle therapy system that irradiates a patient's tumor region with a particle beam. More particularly, the invention relates to a particle therapy system that images a target using X-ray irradiation during a treatment time including an irradiation preparation period and an irradiation period with the particle beam.

BACKGROUND ART

It is important for the particle therapy system to verify the tumor position in forming a dose distribution conforming to the shape of the tumor.

Particularly, in order to improve the accuracy of the dose distribution over the tumor region that moves in keeping with body motions such as respiration, there is provided a method for irradiation with the particle beam in synchronism with respiration through measurement of the motion of the chest.

Patent Literature 1 describes a technique whereby a CT image for treatment planning is obtained using a CT scanner preparatory to treatment, the obtained CT image being used to determine the region to be irradiated with the particle beam.

PRIOR ART LITERATURE

Patent Literature

Patent Literature 1: JP-2011-217902-A

SUMMARY OF THE INVENTION

Problem to be Solved by the Invention

In measuring the tumor position, it is possible to verify the tumor position more accurately if that position can be imaged in real time during treatment.

However, the inventors found that if an X-ray imaging device is used to verify the tumor position during treatment, the emitted X-rays are scattered by the patient's body and may lead to error in managing the dose of the particle beam.

Specifically, the error may occur in the following manner:

The X-rays emitted during treatment are scattered by the patient's body. At this point, depending on the direction of their scattering, some of the X-rays enter a dosimeter arranged in an irradiation nozzle. Since the dosimeter cannot distinguish between the scattered X-rays and the particle beam with which the tumor region is irradiated, the dosimeter measures the incident scattered X-rays as an incident particle beam.

Clearly, this makes it difficult to measure the dose of the particle beam accurately. Thus the problem is that it may be difficult to provide highly accurate dose control of the particle beam while securing highly precise dose distribution.

In particular, in a spot scanning setup where the tumor region is divided into multiple spots for individual irradiation with the particle beam, the effect of the scattered X-rays can be significant. For this reason, it is necessary to give more attention to the above-described problem.

An object of the present invention is to provide a particle therapy system that images the tumor region by X-ray irradiation during a treatment time including an irradiation preparation period and an irradiation period with the particle beam, the particle therapy system being capable of managing the dose of the particle beam with high accuracy.

Means for Solving the Problem

In order to solve the above-described problem, there may be adopted, for example, the structures described in the appended claims of this application.

This application includes multiple means for solving the above-described problem, one such means being a particle therapy system including: a particle beam generator for generating a particle beam; an irradiation nozzle arranged in a treatment room and irradiating a target with the particle beam, the irradiation nozzle having a dosimeter arranged at a position passed by the particle beam; a particle beam transport system for communicating the particle beam generator with the irradiation nozzle; an X-ray imaging device arranged in the treatment room and imaging the position of the target through irradiation with X-rays; and a control apparatus for performing control to exclude the measurement result of scattered X-rays derived from the X-ray imaging device from the measurement result obtained using the dosimeter.

Effect of the Invention

According to the present invention, when X-rays are emitted during the treatment time, control is performed so that the measurement result of X-rays is excluded from the measurement result by the dosimeter arranged at a position passed by the charged particle beam in the irradiation nozzle. The structure makes it possible to distinguish between the scattered X-rays and the particle beam, so that the dose of the particle beam can be measured correctly. That in turn permits highly accurate management of the dose of the particle beam.

MODE FOR CARRYING OUT THE INVENTION

Some preferred embodiments of the present invention are explained below by use of the accompanying drawings.

It is assumed that the particle therapy system embodying the present invention utilizes the discrete spot scanning technique whereby the tumor region is divided into minute three-dimensional regions called spots on which the irradiation dose is suitably focused. The particle beam is assumed to include a proton beam, a neutron beam, and a carbon ion beam.

Also, during treatment by the particle beam, particle beam irradiation may be performed at different energy levels so as to form a desired dose distribution over the tumor. To carry out this kind of treatment requires temporarily stopping the irradiation and, while the irradiation is being stopped, getting the particle beam generator to generate a particle beam having a different energy level. In particle beam treatment, the time required to generate a particle beam having a different energy level is also handled as the time required for the treatment. In the ensuing description, the treatment time is assumed to be the sum of the time for particle beam irradiation and the time in which to prepare the particle beam for irradiation.

First Embodiment

The particle therapy system as a first embodiment of the present invention is explained below by use of FIGS. 1 through 4.

Figure 1:
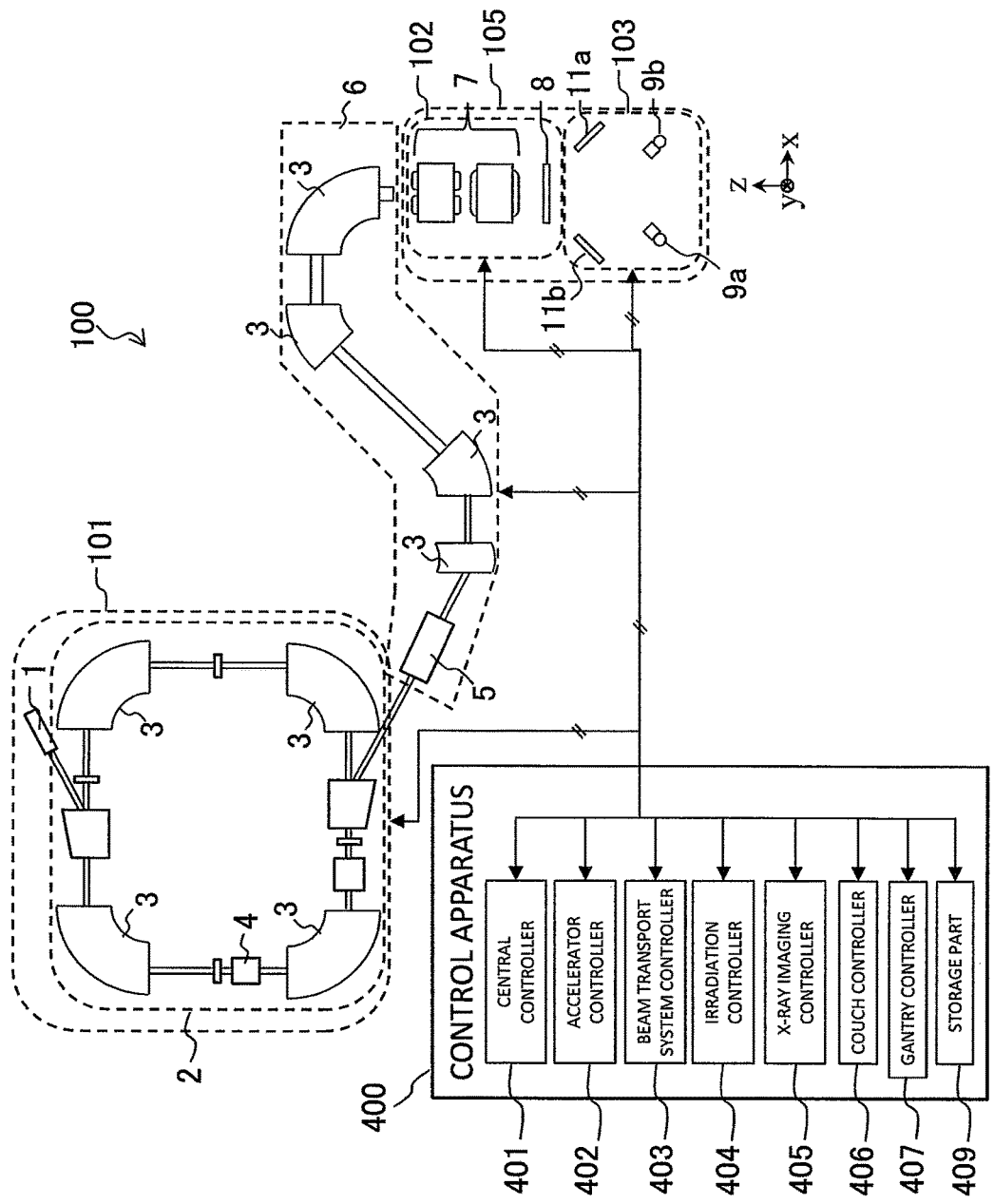
FIG. 1 is a diagram showing an overall structure of a particle therapy system as one embodiment of the present invention.
Figure 2:
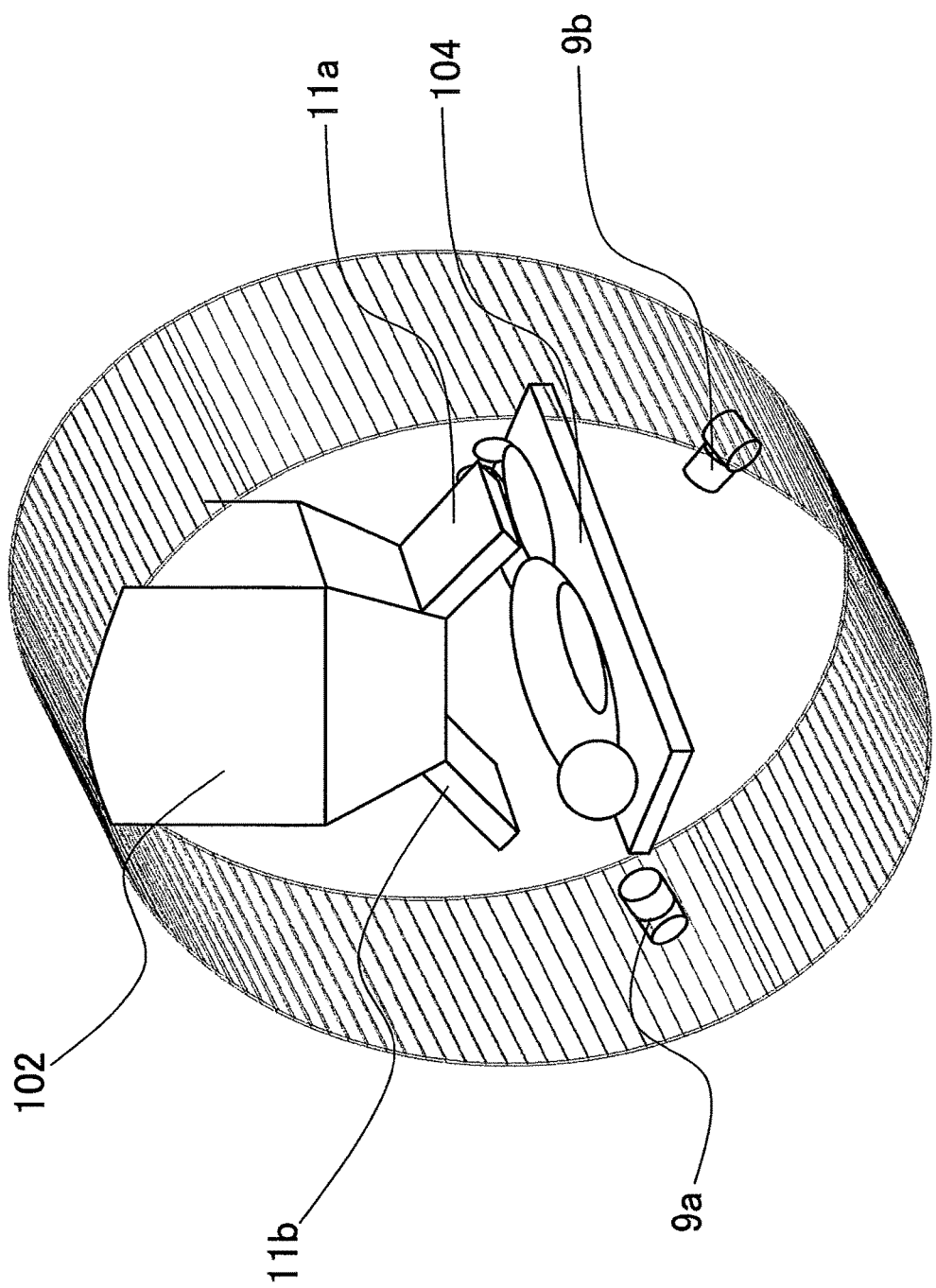
FIG. 2 is a diagram showing an overall structure of a treatment room making up part of the particle therapy system as one embodiment of the present invention.
Figure 3:
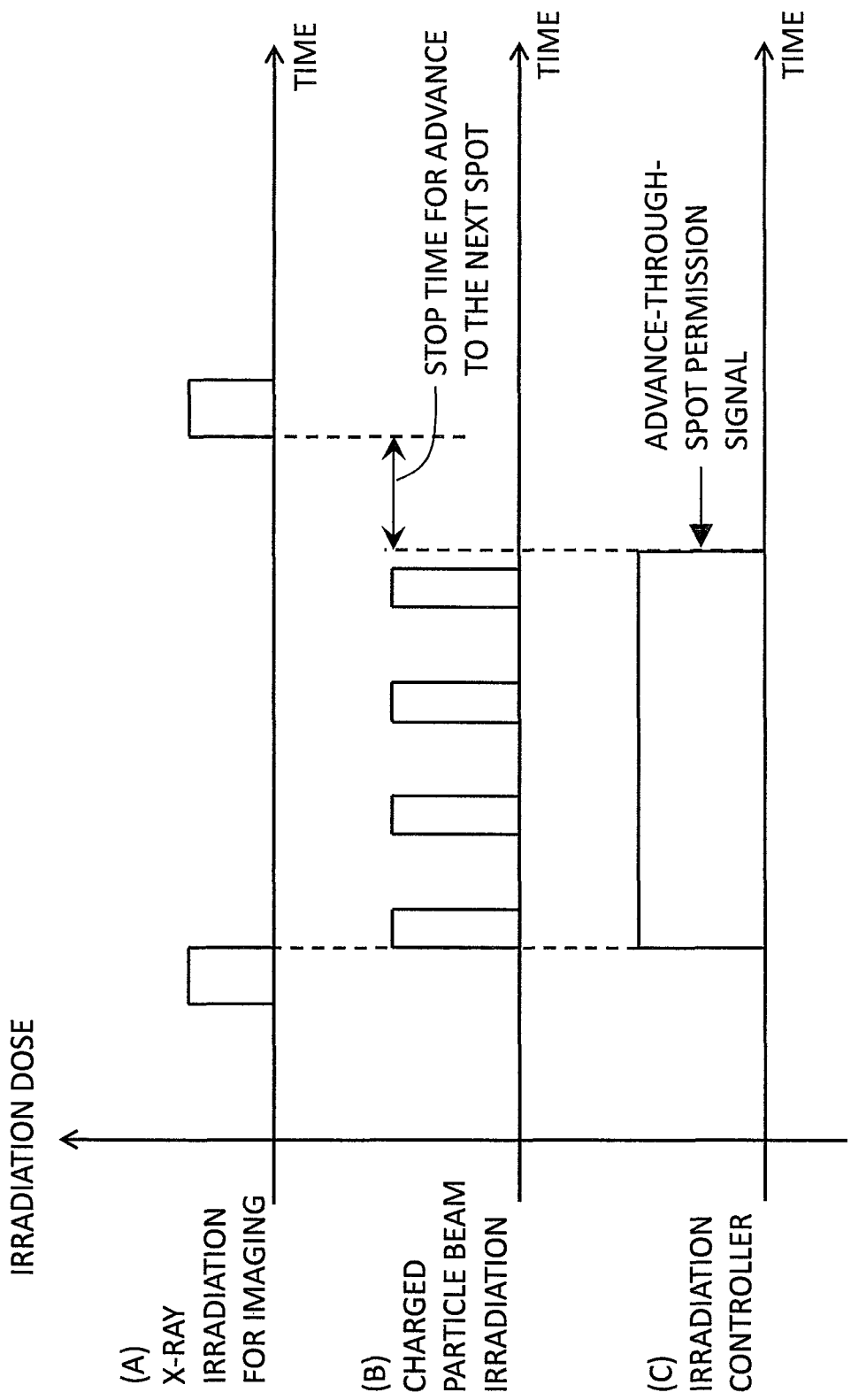
FIG. 3 is a diagram showing the timings of X-ray and particle beam irradiation in effect when the advance of the particle beam to the next spot is stopped at a predetermined time before X-ray irradiation as well as the timing of a signal output from an X-ray imaging controller, at the time of particle beam irradiation by the particle therapy system.
Figure 4:
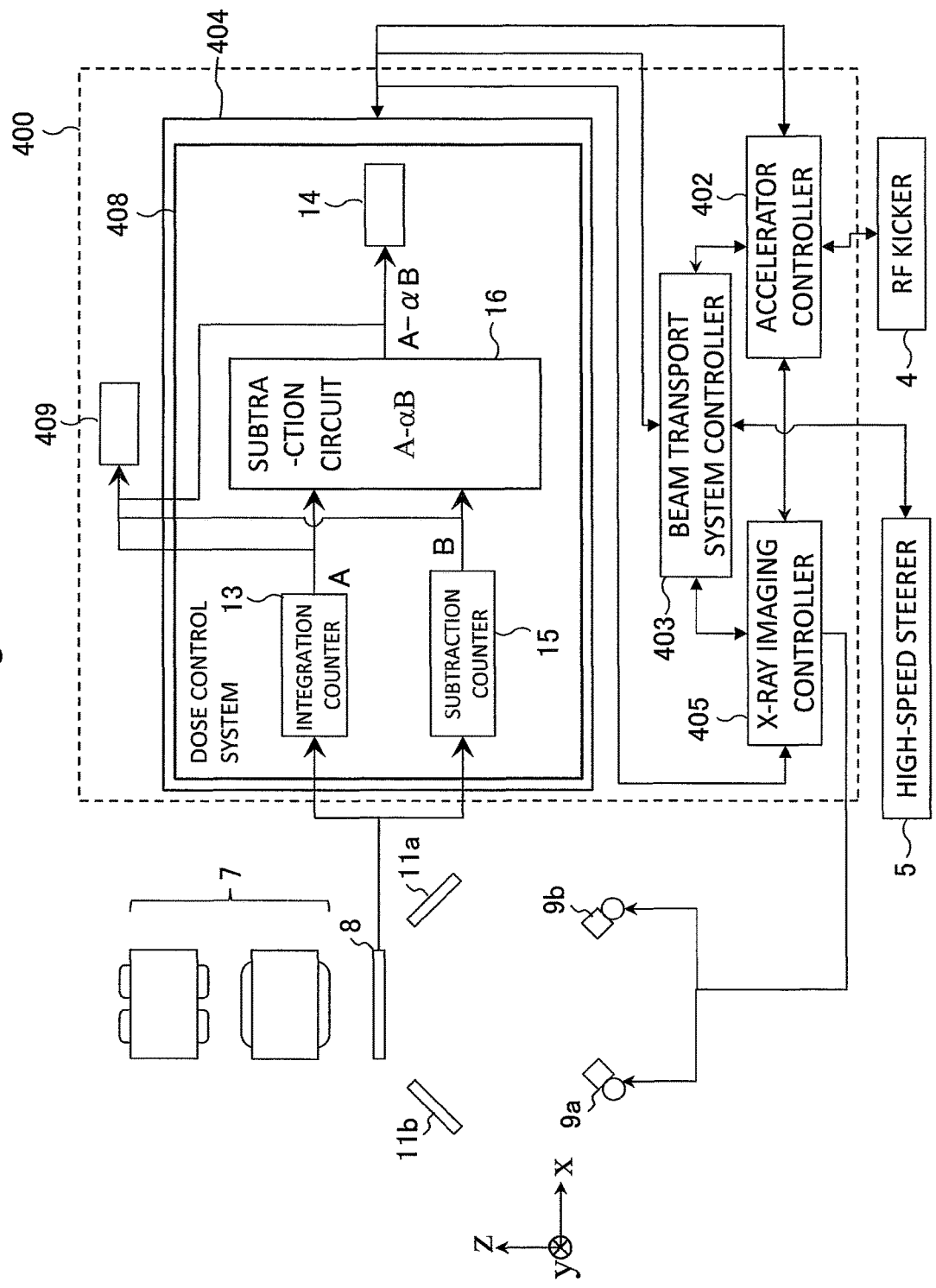
FIG. 4 is a schematic diagram showing typical structures of an irradiation nozzle, an X-ray imaging device, and a control apparatus making up the particle therapy system as one embodiment of the invention.

FIG. 1 is a diagram showing an overall structure of a particle therapy system as the first embodiment of the present invention. FIG. 2 is a diagram showing an overall structure of a treatment room making up part of the particle therapy system as the first embodiment of the present invention. FIG. 3 is a diagram showing the timings of X-ray and particle beam irradiation in effect when the advance of the particle beam to the next spot is stopped at a predetermined time before X-ray irradiation as well as the timing of a signal output from an X-ray imaging controller, at the time of particle beam irradiation by the particle therapy system. FIG. 4 is a schematic diagram showing typical structures of an irradiation nozzle, an X-ray imaging device, and a control apparatus making up the particle therapy system as the first embodiment of the invention.

As shown in FIG. 1, a particle therapy system 100 is mainly composed of a particle beam generator 101, a particle beam transport system 6, a treatment room 105, and a control apparatus 400.

The particle beam generator 101 is primarily made up of an ion source, a pre-accelerator 1 such as a linac, and a synchrotron 2 that is an accelerator.

When particle beam treatment is to be carried out, charged particles generated by the ion source are supplied to the pre-accelerator 1. The pre-accelerator 1 accelerates the charged particles before feeding them to the synchrotron 2. Given the charged particles from the pre-accelerator 1, the synchrotron 2 further accelerates the charged particles up to a predetermined energy level to generate a charged particle beam (particle beam). Also, to extract an orbiting particle beam, the synchrotron 2 incorporates a radio frequency quadruple magnet that changes the stability limit condition of the particle beam and an RF kicker 4 that applies a radio frequency to increase the betatron oscillation amplitude of the particle beam.

Whereas the synchrotron 2 has been cited as a typical accelerator, the synchrotron 2 may alternatively be replaced with an accelerator such as a cyclotron that has no need for the pre-accelerator 1.

The particle beam transport system 6 is mainly composed of a particle beam path, a quadruple magnet, a bending magnet 3, and a high-speed steerer 5. The particle beam path constituted by the particle beam transport system 6 communicates the particle beam generator 101 with an irradiation nozzle 102 installed in a treatment room, to be discussed later. The particle beam generated by the particle beam generator 101 is transported to the treatment room via the particle beam transport system 6.

In a treatment room 105, as shown in FIG. 2, there are provided the irradiation nozzle 102 for irradiating the target with the particle beam, an X-ray imaging device 103 for verifying the tumor position, and a couch (bed) 104 for moving the patient to a position suitable for irradiation.

The treatment room 105 may also be provided integrally with a gantry that may be rotated by a motor or the like. If the gantry is furnished with the irradiation nozzle 102 and with part of the particle beam transport system 6, rotating the gantry allows the patient to be treated in any desired direction. The rotation of the gantry enables the tumor difficult to treat in one direction to be treated effectively.

Returning to FIG. 1, the irradiation nozzle 102 is equipped with two scanning magnets 7 and a dosimeter 8.

The particle beam transported by the particle beam transport system 6 is emitted between the scanning magnets 7 and past the dosimeter 8. The emitted particle beam passing between the scanning magnets 7 excited as per a treatment plan is bent by electromagnetic force for scanning in the X and Y directions, thus forming an irradiation field suitable for the tumor shape.

The dosimeter 8 is interposed between the scanning magnets 7 and the patient in order to measure the irradiation dose as close to the patient as possible. The dosimeter 8 measures the dose of the particle beam passing itself. The measurement values thus obtained are used for dose management.

The X-ray imaging device 103 has X-ray generators 9a and 9b for generating X-rays for imaging that may be emitted in pulses, and X-ray receivers 11a and 11b for detecting the generated X-rays.

The X-ray generators 9a and 9b have their irradiation timings controlled by an X-ray imaging controller 405. These components are arranged in a manner permitting imaging in two axial directions, as shown in FIG. 1. That is, the X-ray generator 9a and the X-ray receiver 11a are arranged opposite to each other across the region where the patient is positioned. In addition, the X-ray receiver 11a is positioned on the side of the irradiation nozzle 102. As with the X-ray generator 9a and X-ray receiver 11a above, the X-ray generator 9b and the X-ray receiver 11b are arranged opposite to each other across the patient's region. Further, the X-ray receiver 11b is positioned on the side of the irradiation nozzle 102. In this setup, a line segment connecting the X-ray generator 9a with the X-ray receiver 11a and a line segment connecting the X-ray generator 9b with the X-ray receiver 11b intersect with each other in the patient's region.

The X-ray imaging device 103 may be arranged alternatively to permit imaging in one axial direction. As another alternative, the X-ray generators and the X-ray receivers may be reversed in their arrangement.

The control apparatus 400 controls the components making up the above-described particle beam generator 101, particle beam transport system 6, rotating gantry, irradiation nozzle 102, X-ray imaging device 103, and the like.

As shown in FIG. 1, the control apparatus 400 is structured to exchange signals with individual controllers such as a central controller 401 and with the particle beam generator 101, particle beam transport system 6, rotating gantry, irradiation nozzle 102, X-ray imaging device 103, and the like. The control apparatus 400 incorporates, in addition to the individual controllers made up of the central controller 401, an accelerator controller 402, a beam transport system controller 403, an irradiation controller 404, an X-ray controller 405, a couch controller 406, and a gantry controller 407, a storage part 409 that stores various parameters and an input part for inputting such parameters.

The control apparatus 400 of this embodiment uses the central controller 401 to perform controls such as interlock. The accelerator controller 402 is used to control the components making up the particle beam generator 101, and the beam transport system controller 403 is used to control the components constituting the particle beam transport system 6. Further, the irradiation controller 404 is used to control the irradiation nozzle 102, and the X-ray imaging controller 405 is used to control the X-ray imaging device 103. The couch controller 406 is used to control the components of the couch 104, and the gantry controller 407 is used to control the rotating gantry.

Also, the control apparatus 400 uses the X-ray imaging controller 405 to perform control to separate the timing of particle beam irradiation from the timing of X-ray irradiation.

Furthermore, the control apparatus 400 uses the irradiation controller 404 to perform a computing process that excludes the contribution of scattered X-rays from the measurement result obtained using the dosimeter 8.

Next, the control performed by the X-ray imaging controller 405 in the control apparatus 400 is explained below in detail with reference to FIG. 3.

The X-ray imaging controller 405 outputs signals to the X-ray generators 9a and 9b to cause them to perform X-ray irradiation in pulses (pulse irradiation) at predetermined time intervals in order to image the tumor position continuously, as shown in FIG. 3(A). During a predetermined time period following completion of X-ray irradiation until the next X-ray irradiation (stop time for advance to the next spot), the X-ray imaging controller 405 outputs an advance-through-spot permission signal to the irradiation controller 404. While the advance-through-spot permission signal is being input as shown in FIG. 3(C), the irradiation controller 404 performs particle beam irradiation as indicated in FIG. 3(B) while controlling the beam transport system controller 403 and accelerator controller 402 in such a manner as to update the particle beam irradiation position by replacing the currently irradiated spot with the spot to be irradiated next. When the input of the advance-through-spot permission signal is interrupted, the irradiation controller 404 outputs an advance-through-spot stop signal to the beam transport system controller 403 and accelerator controller 402. Given the advance-through-spot stop signal, the beam transport system controller 403 transmits an excitation signal to the high-speed steerer 5 arranged in the particle beam transport system 6, so as not to update the particle beam irradiation position by replacing the currently irradiated spot with the spot to be irradiated next. Given the advance-through-spot stop signal, the accelerator controller 402 outputs a stop signal to the RF kicker 4.

As described above, the control apparatus 400 cuts off transport of the particle beam to the irradiation nozzle 102 upon receipt of the pre-pulse signal from the X-ray imaging controller 405, thus performing control to separate the timing of particle beam irradiation from the timing of X-ray irradiation.

Next, the structure and control of the irradiation controller 404 are explained in detail by use of FIG. 4.

As shown in FIG. 4, the irradiation controller 404 includes a dose control system 408 that excludes the contribution of scattered X-rays from the measurement result obtained using the dosimeter 8.

The dose control system 408 is mainly composed of the dosimeter 8 that outputs electrical signals when measuring the particle beam and X-rays, an integration counter 13 that integrates signals from the dosimeter 8, a subtraction integration counter 15 that integrates signals from the dosimeter 8 only while particle beam irradiation is not being performed, a subtraction computing part 16 that performs the computation of A−αB based on an integrated value A output from the integration counter 13 and on an integrated value B from the subtraction integration counter 15, and a dose expiration determining part 14 that determines whether the planned dose has been emitted. The computation results from the integration counter 13, subtraction integration counter 15, and subtraction computing part 16 are stored into the storage part 409.

The constant α used by the subtraction computing part 16 is a coefficient for making A−αB=0 while particle beam irradiation is not being carried out. As such, the constant α is worked out before the particle therapy system starts to be operated. For this embodiment, the constant α is 1.

The computing process performed by the dose control system 408 is explained below with regard to two cases: where X-rays are emitted (while particle beam irradiation is stopped), and where the particle beam is emitted (while X-ray irradiation is stopped).

Explained first is the case where the X-ray generators 9a and 9b are used to perform pulse irradiation in order to image the tumor position.

While X-rays are being emitted by the X-ray generators 9a and 9b, the emitted X-rays are scattered in various directions owing to the presence of the patient's body and other factors. The dosimeter 8 arranged in the irradiation nozzle 102 remains active regardless of particle beam irradiation being performed or stopped. For this reason, the dosimeter 8 measures the scattered incident X-rays without distinction from the particle beam transported by the beam transport system 6. The particle beam and X-rays measured by the dosimeter 8 are converted to electrical signals which, upon receipt by the integration counter 13 and subtraction integration counter 15, are integrated thereby. If the integrated value from the integration counter 13 is assumed to be A and the integrated value from the subtraction integration counter 15 is assumed to be B, the integrated values A and B from the integration counter 13 and subtraction integration counter 15 are output to the subtraction computing part (subtracting part) 16. The subtraction computing part 16 performs the computation of A−αB. The computation result from the subtraction computing part 16 is output to the dose expiration determining part 14 that determines whether the irradiation dose has reached a planned value. Here, the dose expiration determining part 14 performs dose control to determine whether a predetermined dose has been emitted.

Explained next is the case where X-ray pulse irradiation is stopped and particle beam irradiation is carried out.

Since the particle beam passes through the dosimeter 8 when emitted, the dosimeter 8 measures the passing particle beam. The dosimeter 8 outputs an electrical signal reflecting the measured particle beam. The electrical signal is received by both the integration counter 13 and the subtraction integration counter 15. At this point, the integration counter 13 integrates the signal, while the subtraction integration counter 15 does not integrate the signal because this counter is active only during X-ray irradiation. It follows that the integrated value B from the subtraction integration counter 15 is 0. The integrated values A and B from the counters 13 and 15 are output to the subtraction computing part 16 that performs the computation of A−αB (provided B=0). The computation performed here is the same as when X-ray pulse irradiation is carried out.

In this manner, the dose control system 408 of this embodiment uses the subtraction integration counter 15 to acquire the measured value derived from the scattered X-rays. The integrated value derived from the scattered X-rays can thus be subtracted from the integrated value of the dosimeter 8, which permits acquisition of the measured value based on the irradiation dose of the actual particle beam.

Whereas the subtraction integration counter 15 is structured to be in operation only during X-ray irradiation, this operation is controlled by use of a signal output in accordance with the excitation of the high-speed steerer 5. The stop time of particle beam irradiation is equal to the time in which the high-speed steerer 5 arranged in the beam transport system 6 is being excited, and X-ray irradiation is performed during that time period. For this reason, the use of the signal reflecting the excitation status of the high-speed steerer 5 allows the signal integration at the time of X-ray irradiation to be carried out selectively.

The particle therapy system of this embodiment offers the following effects:

First, because the X-ray imaging controller 405 in the control apparatus 400 performs control to separate the timing of particle beam irradiation from the timing of X-ray irradiation, there is no time period in which the dosimeter 8 measures the two kinds of irradiation simultaneously. This eliminates the possibility of making an erroneous dose count that is attributable to the presence of scattered X-rays. And since the advance of the particle beam to the next spot is stopped at a predetermined time before X-ray irradiation, there is no need for a high-speed blocking mechanism for blocking the particle beam at high speed, which provides a simplified device structure.

Furthermore, the dose control system 408 included in the irradiation controller 404 of the control apparatus 400 subtracts the integrated value derived from the scattered X-rays from the integral value of the dosimeter 8 to obtain the measured value based on particle beam irradiation. This allows the dose of the particle beam to be controlled more accurately than before.

In addition, the particle therapy system of this embodiment can continue highly accurate dose control even if irradiation is temporarily interrupted because of the patient's body movement or other factors during treatment, the interruption being followed by resumed treatment.

Consider, for example, the case in which the tumor region is significantly moved because of the patient's body movement during treatment with the particle beam. In that case, the irradiation is interrupted. Before the irradiation can be resumed, it is necessary to again establish the patient's position using X-ray imaging. At this point, if the dosimeter 8 erroneously measures the scatter component of the X-rays emitted for positioning, there is a possibility that error may occur in dose control before and after the interruption of irradiation. According to this embodiment, such error will not take place because the timing of particle beam irradiation is separated from the timing of X-ray irradiation and because the measured dose derived from the particle beam can be acquired. Highly precise dose control can thus be maintained even if there occurs an irradiation interruption.

It has been explained that the timing at which the beam transport system controller 403 transmits the excitation signal to the high-speed steerer 5 is made the same as the timing at which the pre-pulse signal is received from the X-ray imaging controller 405. Alternatively, the timing at which to stop particle beam irradiation may be stored in the control apparatus 400 in order to the separate the timing of particle beam irradiation from the timing of X-ray irradiation.

The signal for activating the subtraction integration counter 15 may be any signal as long as it indicates the state of particle beam emission being stopped. For example, it is possible to use a stop signal for the RF kicker 4 arranged in the synchrotron 2 in connection with the extraction of the beam therefrom, or an excitation stop signal for the high-speed quadruple magnet.

Second Embodiment

Figure 5:
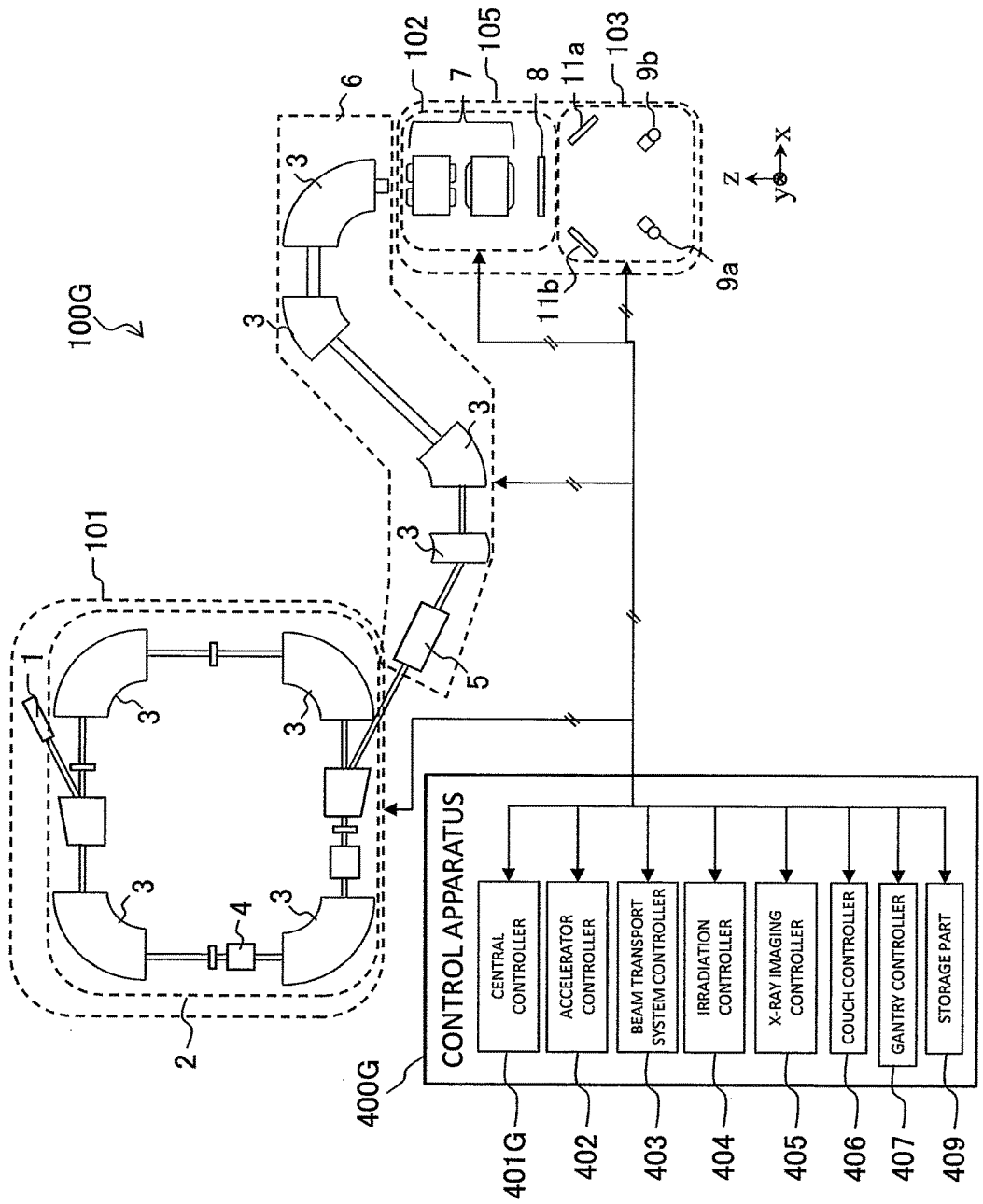
FIG. 5 is a diagram showing an overall structure of another particle therapy system as one embodiment of the present invention.
Figure 6:
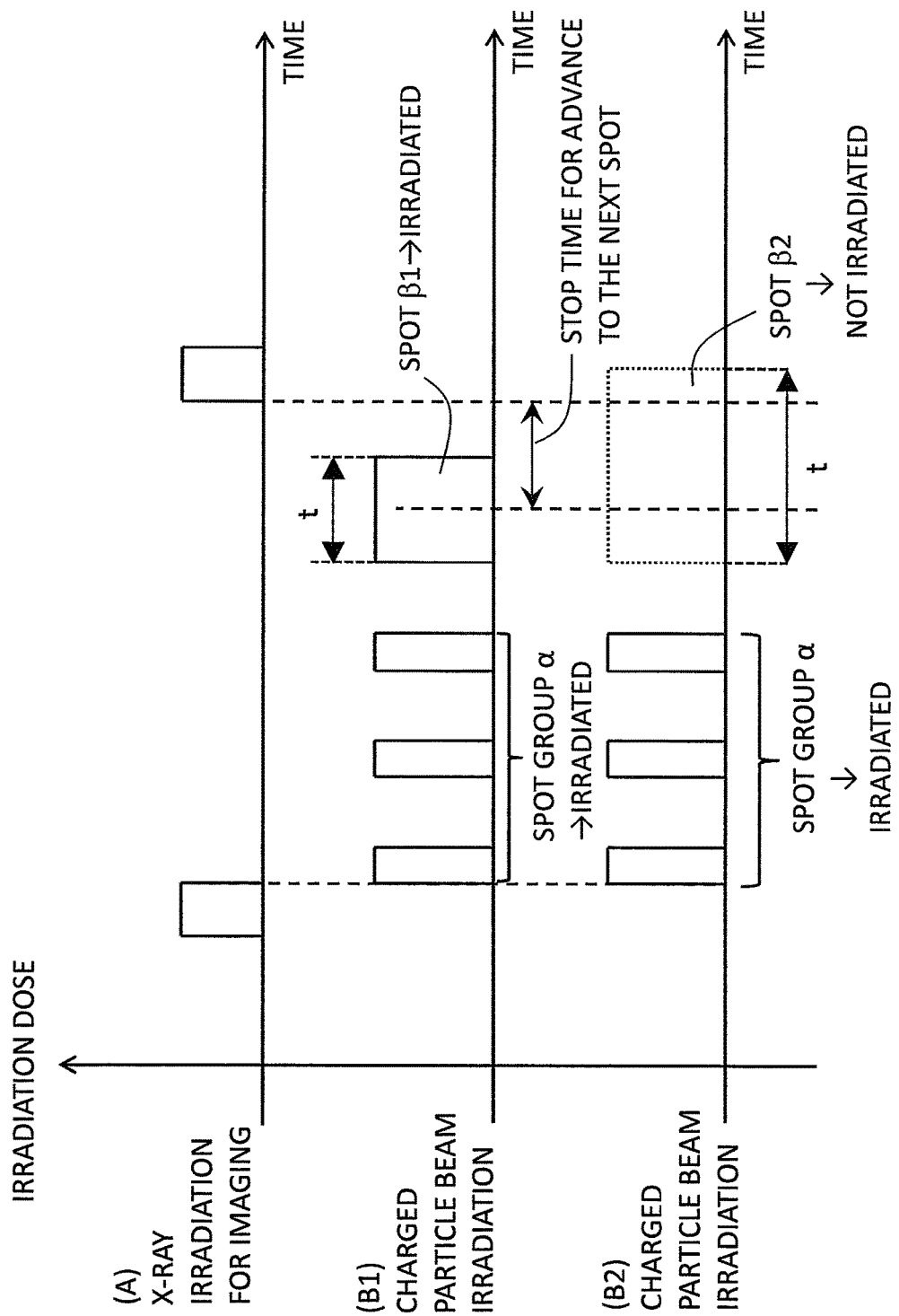
FIG. 6 is a diagram showing typical parameters for determining whether or not to perform particle beam irradiation with the particle therapy system as one embodiment of the invention.

The particle therapy system as a second embodiment of the present invention is explained below with reference to FIGS. 5 and 6. FIG. 5 is a diagram showing an overall structure of another particle therapy system as the second embodiment of the present invention. FIG. 6 is a diagram showing typical parameters for determining whether or not to perform particle beam irradiation with the particle therapy system as the second embodiment of the invention.

A particle therapy system 1000 as the second embodiment shown in FIG. 5 has a control apparatus 400G in which the central controller 401 arranged in the control apparatus 400 of the particle therapy system 100 of the first embodiment shown in FIG. 1 is replaced with a central controller 401G.

Specifically, the central controller 401G in the control apparatus 400G of the particle therapy system 100G of the second embodiment is structured to supplement the control function performed by the central controller 401 of the first embodiment with the function of controlling particle beam irradiation based on a time period estimated to elapse from start to finish of particle beam emission to each spot, the estimation being repeated multiple times during treatment.

The structures and functions of the second embodiment that are the same as those of the first embodiment will not be discussed further. The differences between the two embodiments will be explained in detail.

Before the start of irradiation of a spot, the central controller 401G computes an estimated time t from start to finish of irradiation of that spot. On the basis of the estimated time t computed beforehand, the central controller 401G determines whether the timing of particle beam irradiation overlaps with the timing of X-ray irradiation before irradiation of the spot is finished.

For example, as shown in FIG. 6, the accelerator controller 402 and beam transport system controller 403 are controlled to emit the particle beam to a spot group α (B1 and B2) or to a spot β1 (B1) where it is determined that the timing of particle beam irradiation will not overlap with the timing of X-ray irradiation. On the other hand, the accelerator controller 402 and beam transport system controller 403 are controlled not to emit the particle beam to a spot β2 (shown B2) where it is determined that the timing of particle beam irradiation will overlap with the timing of X-ray irradiation.

It should be noted here that the dose of particle beam irradiation varies from one spot to another and that an intra-spot average beam current varies within a predetermined range. The combination of these factors determines the time of spot irradiation. The second embodiment thus sets the stop time for advance to the next spot with such a margin that even if the highest dose of particle beam irradiation is combined with the smallest intra-spot average beam current, the timing of particle beam irradiation can be separated from the timing of X-ray irradiation.

In cases other than where the highest dose of particle beam irradiation is combined with the smallest intra-spot average beam current, there exists an extra stop time for advance to the next spot. For this reason, the stop time for advance to the next spot may be set to be shorter than where the highest dose of particle beam irradiation is combined with the smallest intra-spot average beam current. With this setting, particle beam irradiation can be separated from X-ray irradiation at almost all timings.

In any case, the second embodiment provides the effects offered by the first embodiment over a shorter extension of the treatment time than the first embodiment.

To compute the estimated time requires obtaining the intra-spot average beam current. The methods for acquiring the average beam current include one involving the use of values computed previously based on a model, and one involving the use of measured values of the beam current for irradiated spots.

Third Embodiment

Figure 7:
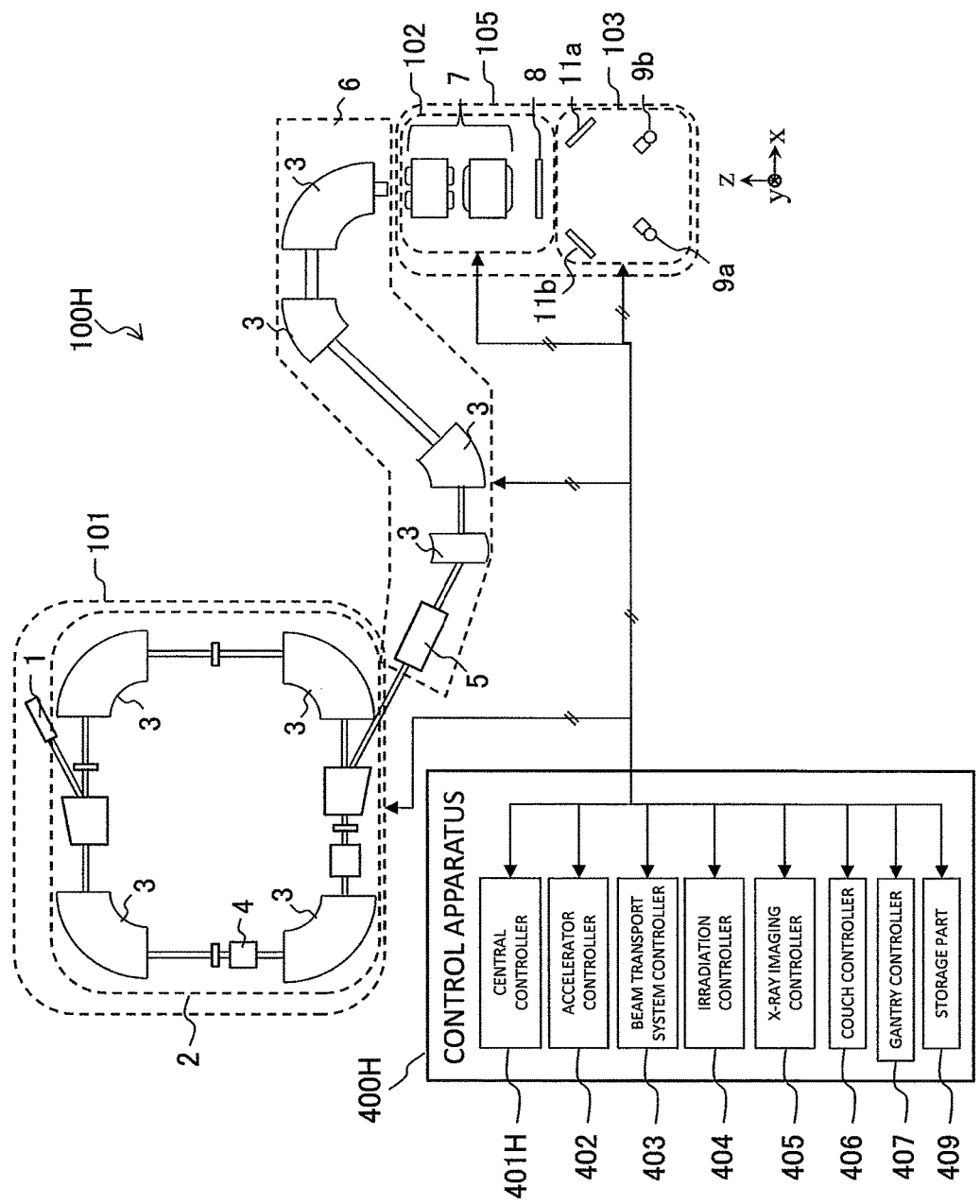
FIG. 7 is a diagram showing an overall structure of another particle therapy system as one embodiment of the present invention.
Figure 8:
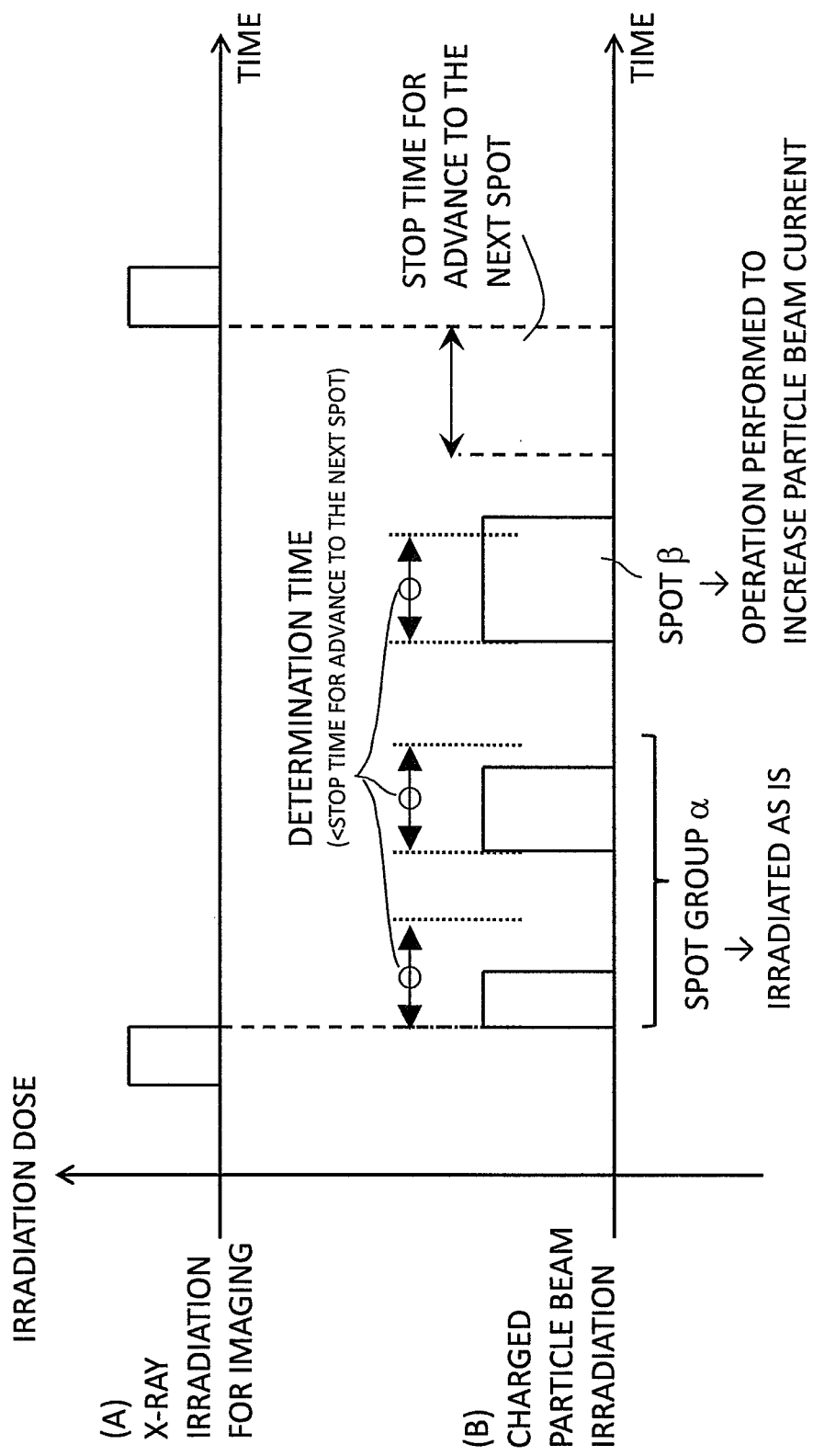
FIG. 8 is a diagram showing typical parameters for determining whether or not to perform particle beam irradiation with the particle therapy system as one embodiment of the invention.

The particle therapy system as a third embodiment of the present invention is explained below with reference to FIGS. 7 and 8. FIG. 7 is a diagram showing an overall structure of another particle therapy system as the third embodiment of the present invention. FIG. 8 is a diagram showing typical parameters for determining whether or not to perform particle beam irradiation with the particle therapy system as the third embodiment of the invention.

A particle therapy system 100H as the third embodiment shown in FIG. 7 has a control apparatus 400H in which the central controller 401 arranged in the control apparatus 400 of the particle therapy system 100 of the first embodiment is replaced with a central controller 401H.

Specifically, the central controller 401H in the control apparatus 400H of the particle therapy system 100H of the third embodiment is structured to supplement the control function performed by the central controller 401 of the first embodiment with the function of controlling particle beam irradiation using the value of a time period measured from start to finish of irradiation of each spot, the measurement being repeated multiple times during treatment.

The structures and functions of the third embodiment that are the same as those of the first embodiment will not be discussed further. The differences between the two embodiments will be explained in detail.

At the time of advance through the spot, the central controller 401H measures the time from start to finish of irradiation of each spot and compares the measured value with a determination time stored beforehand in the storage part 409. The determination time is set to be shorter than the stop time for advance to the next spot.

When the measured time is shorter than the determination time, as in the case of a spot group α shown in FIG. 8(B), the advance through the spot is continued without further control being added.

On the other hand, if the measured time is determined to be longer than the determination time as in the case of a spot β shown in FIG. 8(B), then control is performed immediately to increase the particle beam current to be extracted from the particle beam generator 101. For example, suitable signals are output to the accelerator controller 402 and beam transport system controller 403 in such a manner that the particle beam may be again generated from the ion source to increase the particle beam orbiting in the synchrotron 2, that the output of the RF kicker 4 for extracting the orbiting particle beam may be increased, or that control may be performed to do both.

The third embodiment performs control to raise the particle beam current when the measured time of a given spot becomes longer than the predetermined time, thus permitting advance through the spot while keeping the time of spot irradiation short. That in turn makes it possible to advance through the spot over a spot irradiation time that is shorter than the stop time for advance to the next spot. The process by which particle beam irradiation is separated from X-ray irradiation thus provides extra time margin. That is, the third embodiment provides the effects offered by the first embodiment more reliably than the latter.

Fourth Embodiment

Figure 9:
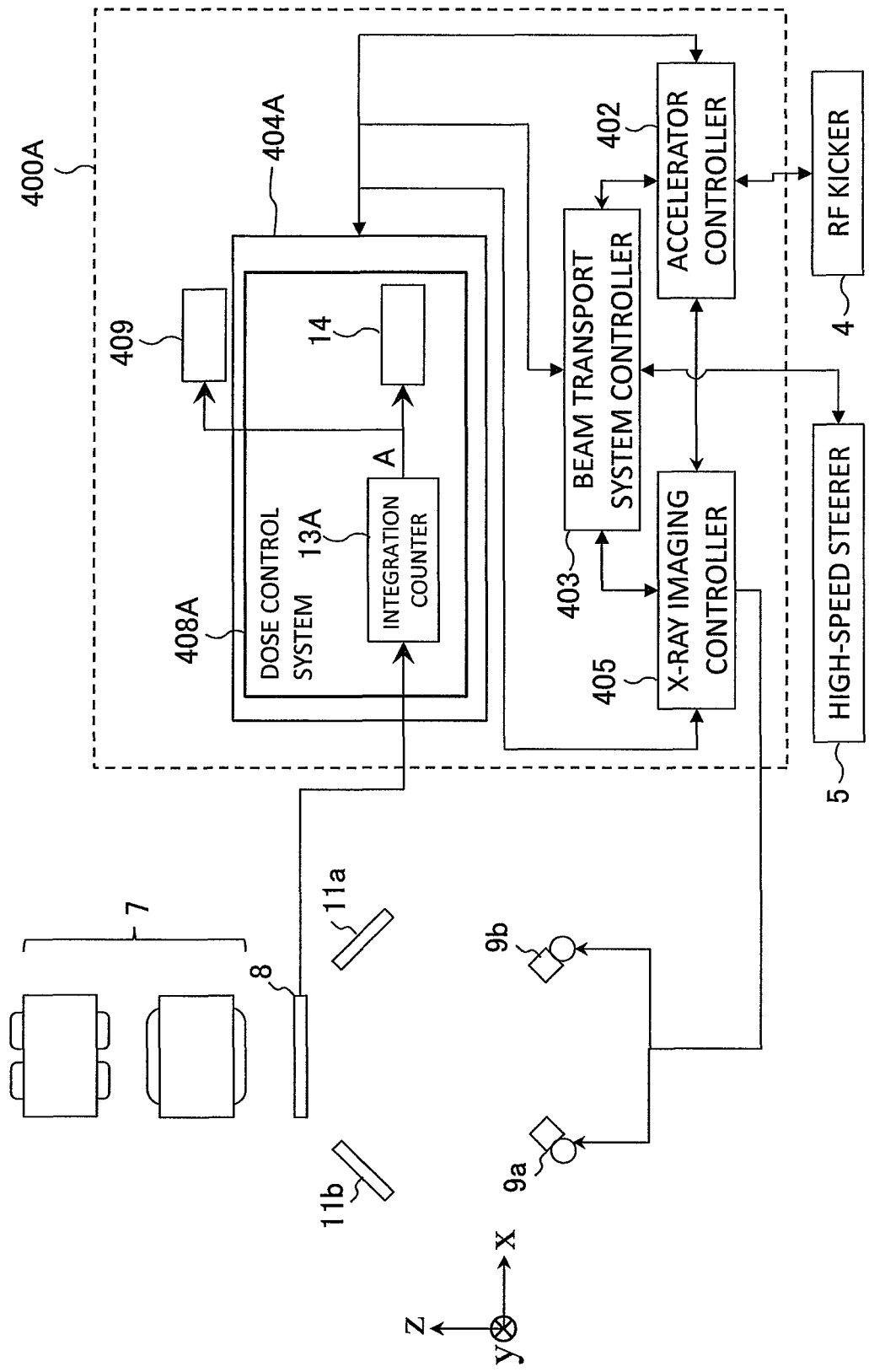
FIG. 9 is a schematic diagram showing other typical structures of the irradiation nozzle, X-ray imaging device, and control apparatus making up the particle therapy system as one embodiment of the invention.

The particle therapy system as a fourth embodiment of the present invention is explained below with reference to FIG. 9. FIG. 9 is a schematic diagram showing other typical structures of the irradiation nozzle, X-ray imaging device, and control apparatus making up the particle therapy system as the fourth embodiment of the invention.

The particle therapy system as the fourth embodiment has a structure in which the dose control system 408 of the irradiation controller 404 arranged in the control apparatus 400 of the particle therapy system 100 as the first embodiment is replaced with a dose control system 408A.

Specifically, as shown in FIG. 9, the dose control system 408A in the irradiation controller 404A of the control apparatus 400A of the fourth embodiment does not have the subtraction integration counter 15 and subtraction computing part 16 that are included in the dose control system 408 of the first embodiment shown in FIG. 1. The dose control system 408A is included in the irradiation controller 404A furnished in the control apparatus 400A. The structures and functions of the fourth embodiment that are the same as those of the first embodiment will not be discussed further. The differences between the two embodiments will be explained in detail.

In the fourth embodiment, the control apparatus 400A also uses the X-ray imaging controller 405 to perform control to separate the timing of particle beam irradiation from the timing of X-ray irradiation.

As shown in FIG. 9, the dose control system 408A of the fourth embodiment is mainly composed of an integration counter 13A that integrates signals from the dosimeter 8 and a dose expiration determining part 14 that determines whether the planned dose has been emitted. The integration counter 13A is connected directly with the dose expiration determining part 14.

The integration counter 13A is structured to integrate signals from the dosimeter 8 only during particle beam irradiation.

The computing process performed by the dose control system 408A is explained below with regard to two cases: where X-rays are emitted, and where the particle beam is emitted.

Explained first is the case where the X-ray generators 9 are used to perform pulse irradiation in order to image the tumor position.

Since the dosimeter 8 remains active regardless of particle beam irradiation being performed or stopped, the dosimeter 8 measures the scattered incident X-rays. At this point, an electrical signal reflecting the scattered X-rays thus measured is output from the dosimeter 8 to the integration counter 13A which, however, is stopped and thus does not integrate the signal. For this reason, "0" is output as the integration signal to the dose expiration determining part 14.

On the other hand, while X-ray pulse irradiation is stopped and particle beam irradiation is in progress, the electrical signal reflecting the measured particle beam is output from the dosimeter 8 and integrated by the integration counter 13A. An integrated value A from the integration counter 13A is output to the dose expiration determining part 14 which in turn determines whether the irradiation dose has reached the planned value.

As explained above, the dose control system 408A of the fourth embodiment causes the integration counter 13A to integrate the signals output from the dosimeter 8 only during particle beam irradiation, thus permitting acquisition of the measured value derived from the particle beam only.

In order to let the integration counter 13A operate only during particle beam irradiation, the signal output while the high-speed steerer 5 is being excited is used as the signal to turn off the integration counter 13A.

Besides providing the effects offered by the first embodiment, the fourth embodiment simplifies the configuration of the dose control system because the subtraction integration counter 15 and subtraction computing part 16 are not needed.

Fifth Embodiment

Figure 10:
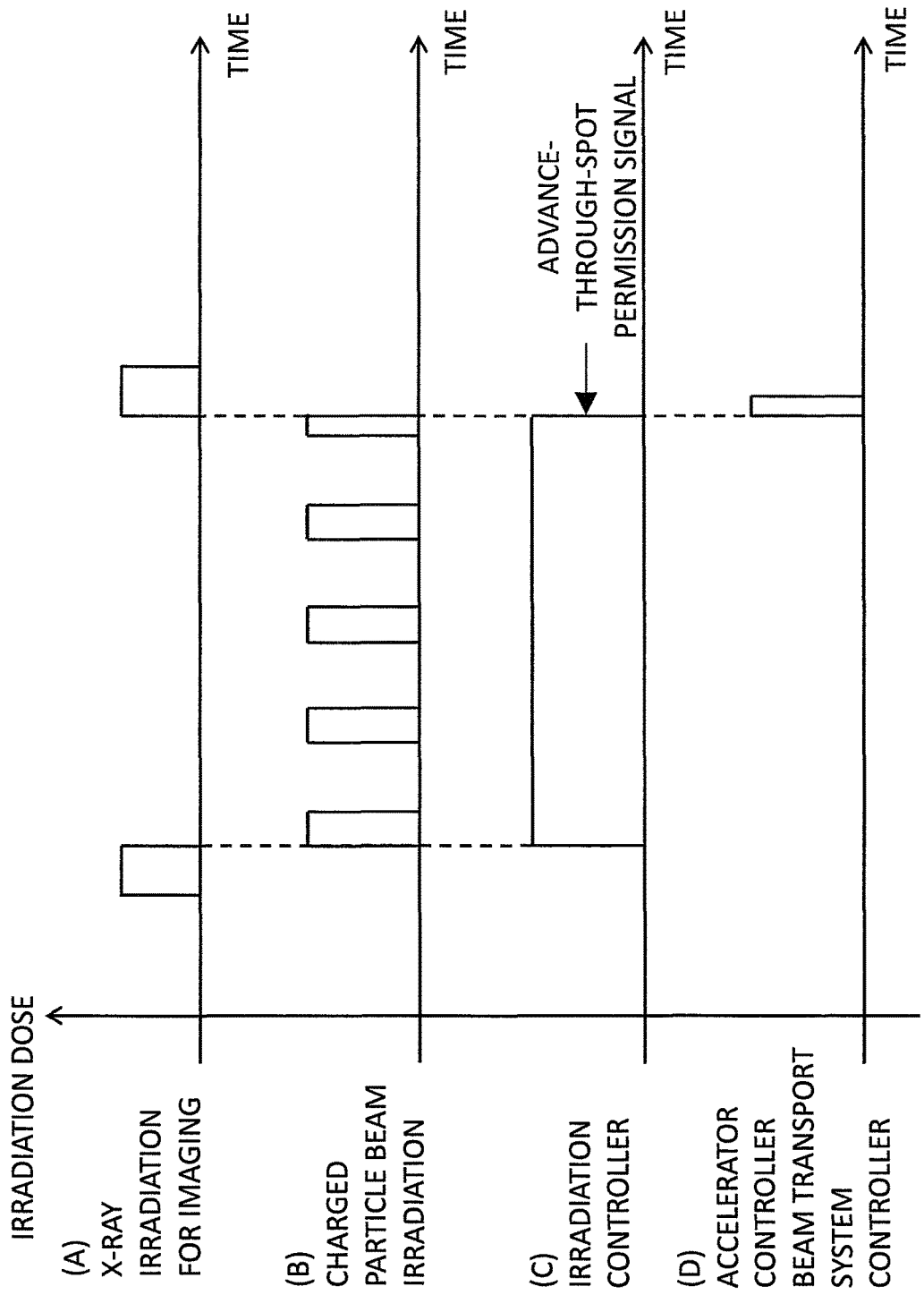
FIG. 10 is a diagram showing the timings of X-ray and particle beam irradiation in effect when particle beam irradiation is stopped the moment X-ray irradiation is started, as well as the timings of signals output from the X-ray imaging controller and an irradiation controller, at the time of particle beam irradiation by the particle therapy system.

The particle therapy system as a fifth embodiment of the present invention is explained below with reference to FIG. 10. FIG. 10 is a diagram showing the timings of X-ray and particle beam irradiation in effect when particle beam irradiation is stopped the moment X-ray irradiation is started, as well as the timings of signals output from the X-ray imaging controller and the irradiation controller, at the time of particle beam irradiation by the particle therapy system.

The particle therapy system as the fifth embodiment has a structure in which the control apparatus 400 in the particle therapy system 100 of the first embodiment is replaced with another control apparatus.

The control apparatus 400 of the first embodiment performs control to stop particle beam irradiation at a predetermined time before the start of X-ray irradiation. By contrast, the control apparatus of the fifth embodiment performs control to separate X-ray irradiation from particle beam irradiation without allowing for the predetermined time therebetween. That is, the particle therapy system of the fifth embodiment has the same structure as the particle therapy system of the first embodiment, but the control apparatuses of the two embodiments perform control differently.

Explained below is how different the control apparatus of the fifth embodiment is from the control apparatus 400 of the first embodiment in performing control. The matters common to the first embodiment will not be discussed further.

In the fifth embodiment, the X-ray imaging controller 405 of the control apparatus outputs an advance-through-spot permission signal to the irradiation controller 404 after X-ray irradiation is stopped until it is resumed, as shown in FIGS. 10(A), 10(B) and 10(C). While the advance-through-spot permission signal is being input, the irradiation controller 404 controls the beam transport system controller 403 and accelerator controller 402 to continue particle beam irradiation. When the input of the advance-through-spot permission signal is interrupted, the irradiation controller 404 outputs an advance-through-spot stop signal to the beam transport system controller 403 and accelerator controller 402, as shown in FIG. 10(D). Given the advance-through-spot stop signal, the beam transport system controller 403 transmits an excitation signal to the high-speed steerer 5 in the particle beam transport system 6 in order to stop particle beam irradiation. Upon receipt of the advance-through-spot stop signal, the accelerator controller 402 outputs a stop signal to the RF kicker 4.

As described above, the particle therapy system as the fifth embodiment stops particle beam irradiation when X-ray pulse irradiation is started and is thus able to separate particle beam irradiation from X-ray irradiation.

The basic structure and operation of the dose control system in the fifth embodiment are the same as in the first embodiment. The difference from the first embodiment is that the X-ray irradiation start signal is used to activate the subtraction integration counter 15. In the fifth embodiment, the signal being output while the high-speed steerer 5 remains excited may also be used to activate the subtraction integration counter 15.

Besides providing the effects offered by the first embodiment, the fifth embodiment minimizes any extension of the treatment time because the predetermined time margin need not be provided to separate particle beam irradiation from X-ray irradiation for imaging.

Sixth Embodiment

The particle therapy system as a sixth embodiment of the present invention is explained below.

The particle therapy system as the sixth embodiment has a structure in which the control apparatus 400A of the particle therapy system 100 as the fourth embodiment is replaced with another control apparatus.

That is, whereas the control apparatus 400A of the fourth embodiment performs control to stop particle beam irradiation at a predetermined time before the start of X-ray irradiation, the control apparatus of the sixth embodiment carries out control to separate X-ray irradiation from particle beam irradiation without allowing for the predetermined time as with the control apparatus of the fifth embodiment. In other words, whereas the particle therapy system as the sixth embodiment has the same structure as the particle therapy system as the fourth embodiment, the control apparatuses of the two embodiments perform control differently.

The dose control system of the sixth embodiment has the same structure as the dose control system 408A of the fourth embodiment shown in FIG. 9. The difference between the dose control system of the sixth embodiment and the dose control system 408A of the fourth embodiment is that the X-ray irradiation start signal is used by the sixth embodiment as the signal to stop the operation of the integration counter 13.

The sixth embodiment minimizes any extension of the treatment time, and simplifies the configuration of the dose control system because the subtraction integration counter 15 and subtraction computing part 16 are not needed.

(Summary of the First Through the Sixth Embodiments)

The first through the sixth embodiments explained above are characterized in that they use the control apparatus to separate the timing of particle beam irradiation from the timing of X-ray pulse irradiation and that they have the dose control system capable of computing the measured value derived from the particle beam alone by subtracting the measured value derived from the scattered X-rays from the measured value of the dosimeter 8. These characteristics amount to eliminating the overlap between measurement periods by separating the timing for measuring the particle beam from the timing for measuring the scattered X-rays. The characteristics also permit acquisition of the measured value derived from the particle beam alone from the measured value of the dosimeter 8.

As a result, highly accurate dose control of the particle beam and a precise distribution of the dose are realized, while the tumor position can be verified in real time by use of X-ray irradiation in pulses.

In particular, the first through the sixth embodiments of the present invention capable of eliminating the measurement error stemming from the X-ray imaging device constitute a significant contribution as a particle therapy system adopting the discrete spot scanning technique or like irradiation techniques that require dose control in increments of very narrow regions.

Although the particle therapy system of each embodiment is assumed to adopt the discrete spot scanning technique, the irradiation controller and dose control system are not limited thereby. Alternatively, the invention may also be applied to particle therapy systems that utilize the raster scanning technique or the wobbler irradiation method involving the use of a scatterer. The timing of particle beam irradiation is separated from the timing of X-ray pulse irradiation by stopping the update of the particle beam irradiation position through provision of the predetermined time margin, or by forcibly stopping particle beam irradiation. Thus the effects remain the same even if the particle beam irradiation technique is not limited to spot scanning.

Other embodiments are also conceivable as a particle therapy system that can verify the tumor position in real time during treatment using X-rays while implementing highly accurate dose control and highly precise dose distribution. These embodiments different in characteristics from the above embodiments are explained below.

Seventh Embodiment

Figure 11:
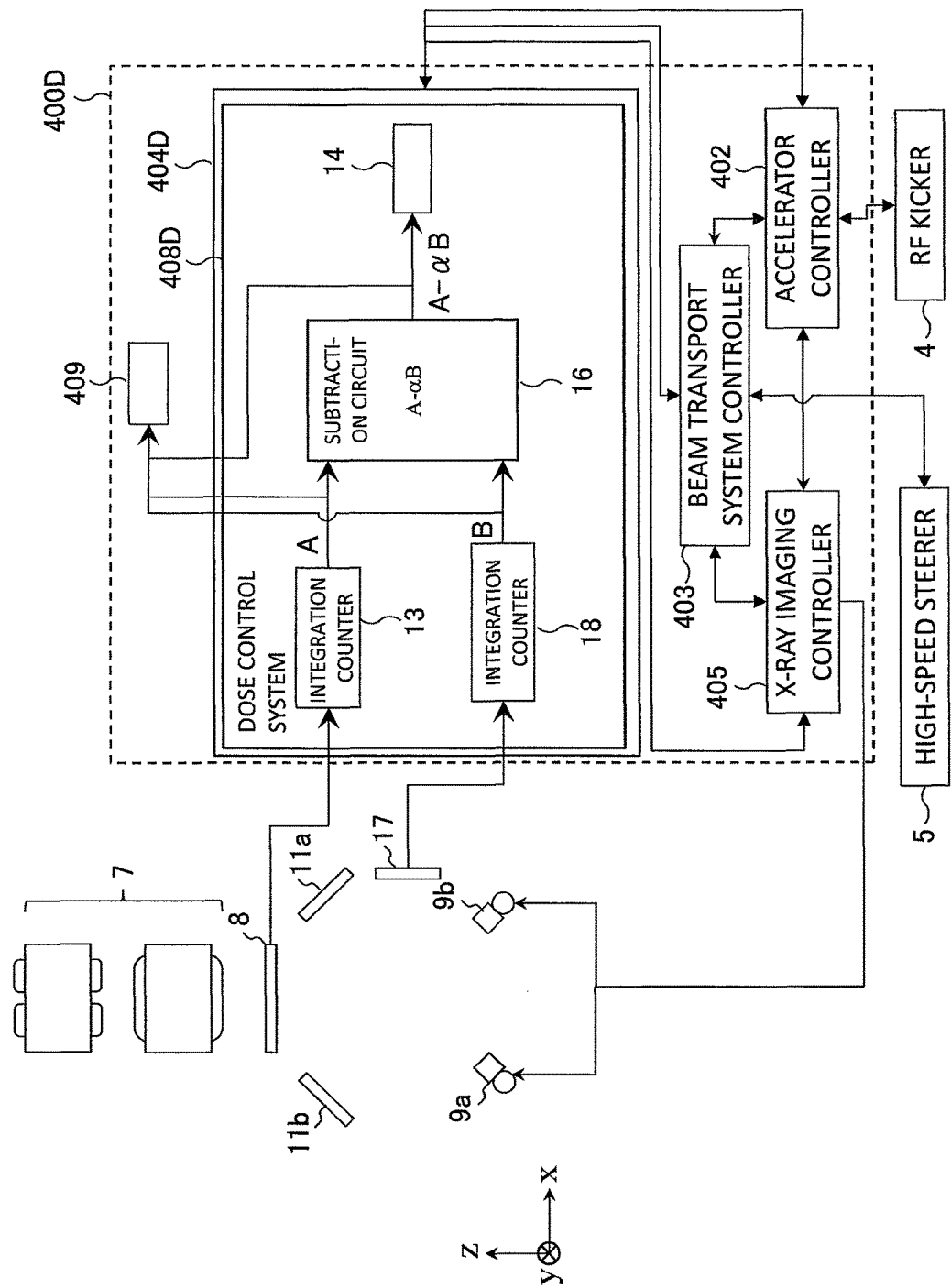
FIG. 11 is a schematic diagram showing other typical structures of the irradiation nozzle, X-ray imaging device, and control apparatus making up the particle therapy system as one embodiment of the invention.

The particle therapy system as a seventh embodiment of the present invention is explained below with reference to FIG. 11. FIG. 11 is a schematic diagram showing other typical structures of the irradiation nozzle, X-ray imaging device, and control apparatus making up the particle therapy system as the seventh embodiment of the invention.

As shown in FIG. 11, in a control apparatus 400D of the particle therapy system as the seventh embodiment, a dose control system 408D in an irradiation controller 404D has a structure in which the dose control system 408 in the irradiation controller 404 of the control apparatus 400 in the particle therapy system 100 shown in FIG. 4 is supplemented structurally with a scattered X-ray dosimeter (second dosimeter) 17 measuring scattered X-rays and a scattered X-ray counter 18 integrating the measured values from the dosimeter 17.

The particle beam dose of the particle therapy system as the seventh embodiment is measured by subtracting from the integrated value obtained using the dosimeter 8 the integrated value derived from the scattered X-rays measured by the scattered X-ray dosimeter 17.

Specifically, the signal output from the dosimeter 8 is integrated by the integration counter 13, and the signal output from the scattered X-ray dosimeter 17 is integrated by the scattered X-ray dosimeter 18. An integrated value A from the integration counter 13 and an integrated value B from the scattered X-ray integration counter 18 are output to the subtraction computing part 16 that performs the computation of A−αB. The result of the computation of A−αB by the subtraction computing part 16 is output to the dose expiration determining part 14 that determines whether the irradiation dose has reached the planned value.

The seventh embodiment has both the scattered X-ray dosimeter 17 measuring scattered X-rays and the scattered X-ray integration counter 18 integrating the signal from the dosimeter 17, so that there is no need to separate the timing of particle beam irradiation from the timing of X-ray irradiation for imaging. The seventh embodiment thus simplifies the scheme of particle beam irradiation control and the dose control system.

The technique for particle beam irradiation may also be the above-mentioned raster scanning. The method for X-ray irradiation is not limited to pulse irradiation.

Eighth Embodiment

Figure 12:
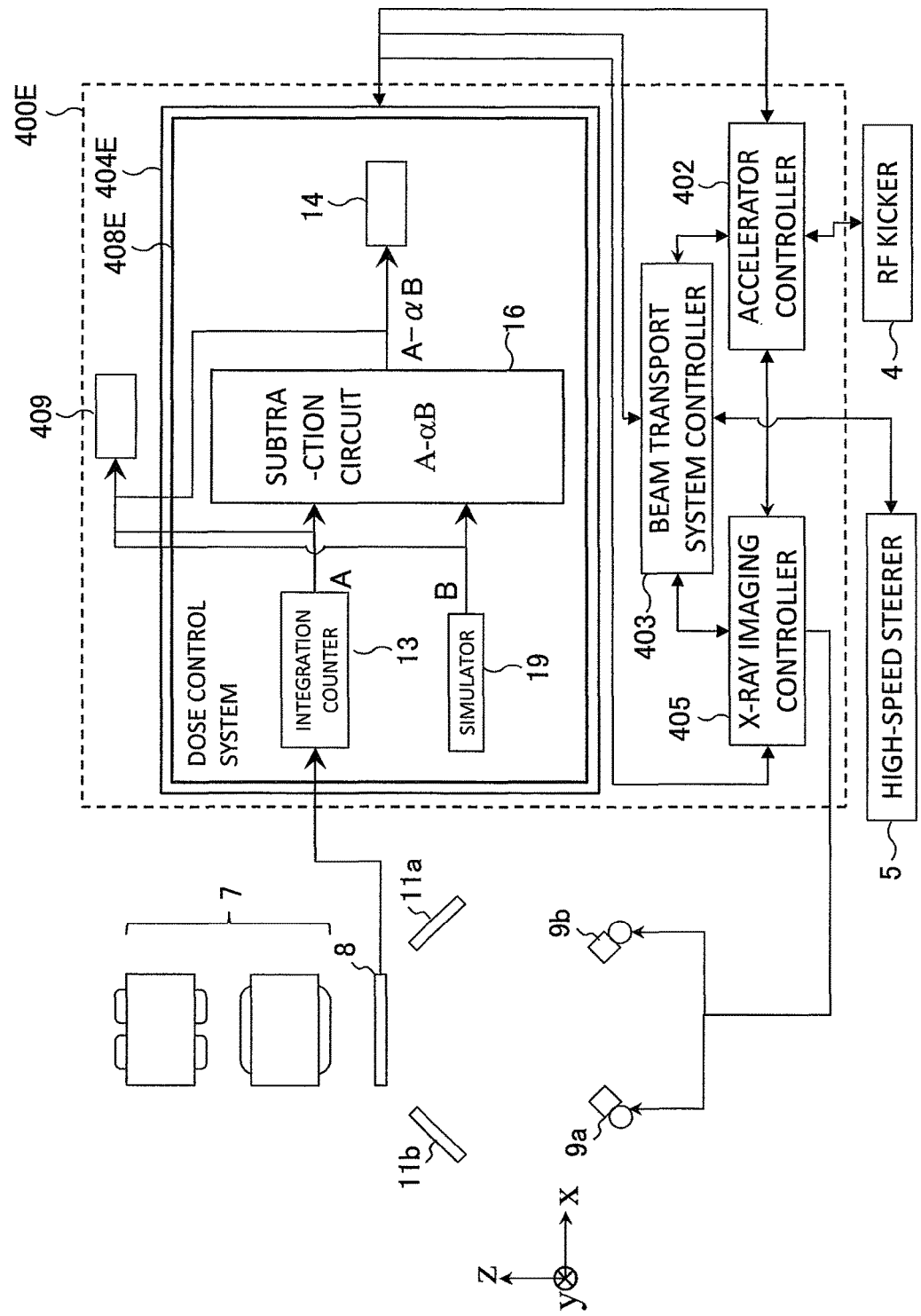
FIG. 12 is a schematic diagram showing other typical structures of the irradiation nozzle, X-ray imaging device, and control apparatus making up the particle therapy system as one embodiment of the invention.

The particle therapy system as an eighth embodiment of the present invention is explained below with reference to FIG. 12. FIG. 12 is a schematic diagram showing other typical structures of the irradiation nozzle, X-ray imaging device, and control apparatus making up the particle therapy system as the eighth embodiment of the invention.

In the eighth embodiment, the structure composed of the scattered X-ray dosimeter 17 shown in the seventh embodiment and of the scattered X-ray integration counter 18 integrating the signals from the dosimeter 17 is replaced with a scattered X-ray simulator 19 outputting to the subtraction computing part 16 a signal simulating the scattered X-rays measured by the dosimeter 8.

In the control apparatus 400G of the particle therapy system as the eighth embodiment, a dose control system 408G in an irradiation controller 404G measures the dose of the particle beam by subtracting the integrated value of the signals output from the scattered X-ray simulator 19, from the integrated value of the signals output from the dosimeter 8, as shown in FIG. 12.

Where the scattered X-ray simulator 19 is used, X-rays for imaging are emitted in advance of treatment and the amount of scattered X-rays is measured in what is known as background measurement. On the basis of the result of the background measurement, the scattered X-ray simulator 19 outputs a simulation signal of the scattered X-rays in interlocking relation with X-ray irradiation. For example, the scattered X-ray simulator 19 outputs the simulation signal to the subtraction computing part 16 only during the period of X-ray irradiation.

The eighth embodiment provides the same effects offered by the seventh embodiment without resorting to the structure made up of the scattered X-ray dosimeter 17 and scattered X-ray integration counter 18 for measuring scattered X-rays.

Ninth Embodiment

Figure 13:
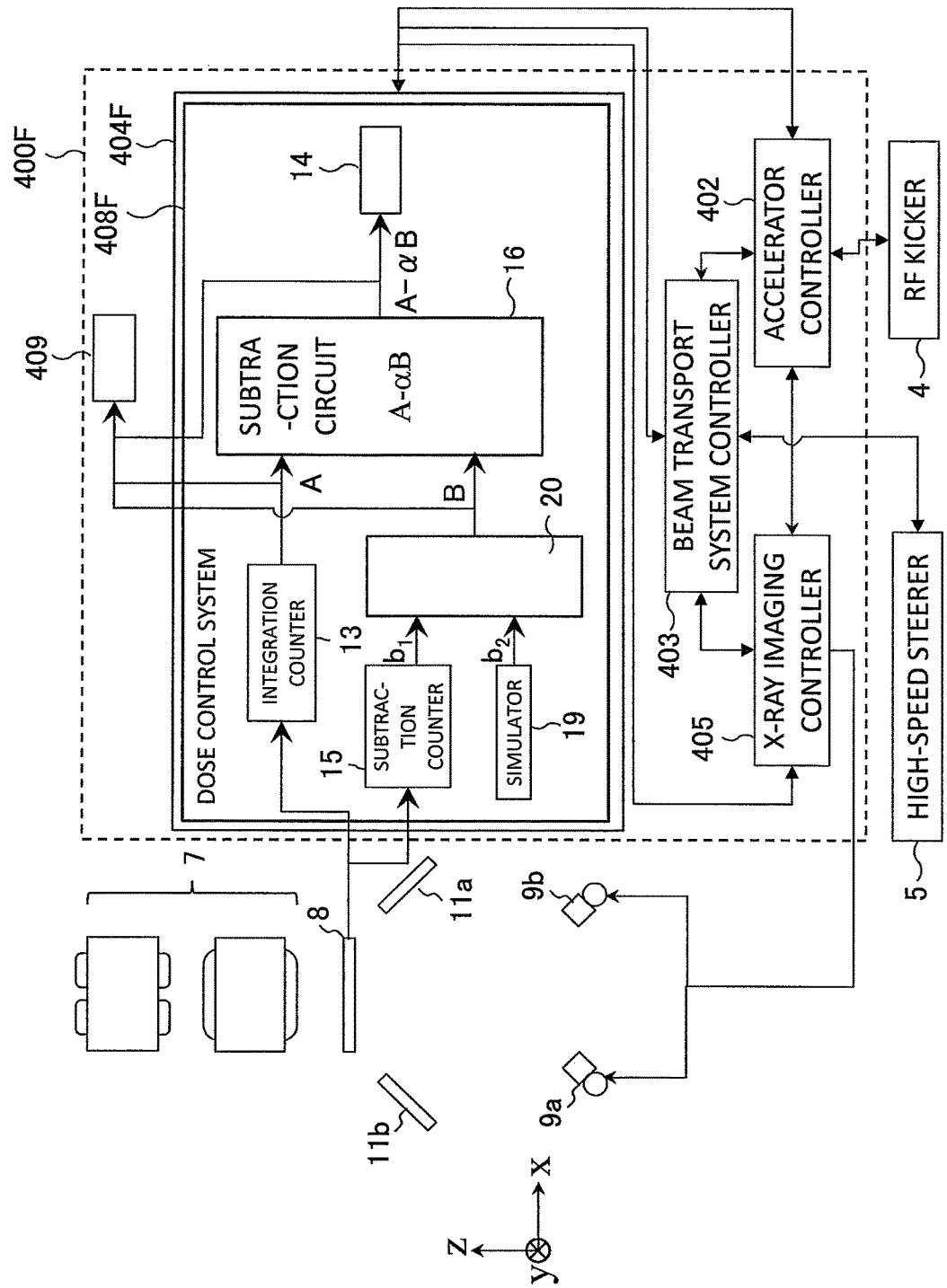
FIG. 13 is a schematic diagram showing other typical structures of the irradiation nozzle, X-ray imaging device, and control apparatus making up the particle therapy system as one embodiment of the invention.

Next, the particle therapy system as a ninth embodiment of the present invention is explained below with reference to FIG. 13. FIG. 13 is a schematic diagram showing other typical structures of the irradiation nozzle, X-ray imaging device, and control apparatus making up the particle therapy system as the ninth embodiment of the invention.

The ninth embodiment has a structure in which the scattered X-ray simulator explained in connection with the eighth embodiment is incorporated in the dose control system explained in conjunction with the first embodiment.

As shown in FIG. 13, the particle therapy system as the ninth embodiment has the subtraction integration counter 15 and scattered X-ray simulator 19 connected to the subtraction computing part 16 via an input selector 20.

The input selector 20 included in the dose control system 408F of the irradiation controller 404F in the control apparatus 400F of the ninth embodiment selects the source of the signal to be output to the subtraction computing part 16 in accordance with irradiation status of the particle beam. That is, during the period in which the particle beam is emitted, the input selector 20 selects an integrated value b2 from the scattered X-ray simulator 19 over an integrated value b1 from the subtraction integration counter 15, the selected integrated value b2 being output as an output value B to the subtraction computing part 16. On the other hand, during the period in which the signal indicative of the high-speed steerer 5 being excited is output, i.e., during the period in which the particle beam is not emitted, the input selector 20 outputs the integrated value b1 from the subtraction integration counter 15 to the subtraction computing part 16 as the output value B. And as with the first embodiment, the subtraction computing part 16 performs the computing process of A−αB and outputs the result of the computation to the dose expiration determining part 14.

In the ninth embodiment, the dose of the particle beam is measured as follows: the integrated value b1 from the subtraction integration counter 15 and the integrated value b2 from the scattered X-ray simulator 19 are input to the input selector 20. In accordance with irradiation status of the particle beam, either the integrated value b1 or the integrated value b2 is output from the input selector 20 as the output value B to the subtraction computing part 16. In turn, the subtraction computing part 16 performs the computing process.

According to the ninth embodiment, it is not mandatory to separate the timing of particle beam irradiation from the timing of X-ray irradiation. Also, the control system can be simplified, and there is little extension of the treatment time. Because the scattered X-rays are measured by use of the dosimeter 8, the accuracy of dose control by the ninth embodiment is higher than by the eighth embodiment.

Others

It should be understood that the present invention when embodied is not limited to the above-described embodiments and that various modifications, variations and alternatives may be made of the invention.

For example, in the first and other embodiments, the X-ray imaging controller 405 of the control apparatus 400 can perform control to separate the timing of particle beam irradiation from the timing of X-ray irradiation, independently of the irradiation controller 404 performing the computing process of excluding the contribution of scattered X-rays from the measurement result obtained using the dosimeter 8.

In the ninth embodiment, the subtraction integration counter 15 may be replaced with the structure composed of the scattered X-ray dosimeter 17 and scattered X-ray integration counter 18 explained in connection with the seventh embodiment. In this case, during the period in which the particle beam is emitted, the input selector 20 selects the integrated value from the scattered X-ray simulator 19 over the integrated value from the scattered X-ray integration counter 18, the selected integrated value from the scattered X-ray simulator 19 being output to the subtraction computing part 16. On the other hand, during the period in which the particle beam is not emitted, the input selector 20 is arranged to output the integrated value from the scattered X-ray integration counter 18 to the subtraction computing part 16.

Furthermore, what was explained above is the structure in which the controllers in the control apparatus 400 are connected in parallel with one another, the control apparatus 400 outputting signals directly to the relevant controllers. However, this structure is not limitative of the control apparatus. As another example, the central controller may be arranged to control the individual controllers in integrated fashion.

DESCRIPTION OF REFERENCE CHARACTERS

1: Pre-accelerator
2: Synchrotron
3: Bending magnet
4: RF kicker
5: High-speed steerer
6: Particle beam transport system
7: Scanning magnet
8: Dosimeter
9a, 9b: X-ray generator
11a, 11b: X-ray receiver
13, 13A: Integration counter
14: Dose expiration determining part
15: Subtraction integration counter
16: Subtraction computing part (Subtracting part)
17: Scattered X-ray dosimeter (Second dosimeter)
18: Scattered X-ray integration counter
19: Scattered X-ray simulator
20: Selector
100, 1000, 100H: Particle therapy system
101: Particle beam generator
102: Irradiation nozzle 103: X-ray imaging device
104: Couch (Bed)
105: Treatment room
400, 400A, 400D, 400E, 400F, 400G, 400H: Control apparatus
401, 401G, 401H: Central controller
402: Accelerator controller
403: Beam transport system controller
404, 404A, 404D, 404E, 404F: Irradiation controller
405: X-ray imaging controller
406: Couch controller
407: Gantry controller
408, 408A, 408D, 408E, 408F: Dose control system
409: Storage part

The invention claimed is:

1. A particle therapy system comprising:
a particle beam generator for generating a particle beam;
an irradiation nozzle arranged in a treatment room and irradiating a target with the particle beam, the irradiation nozzle having a dosimeter arranged at a position passed by the particle beam;
a particle beam transport system for communicating the particle beam generator with the irradiation nozzle;
an X-ray imaging device arranged in the treatment room and imaging a position of the target through irradiation with X-rays; and
a control apparatus configured to:
stop particle beam irradiation before X-ray irradiation performed by the X-ray imaging device and resume the particle beam irradiation upon completion of the X-ray irradiation by the X-ray imaging device;
exclude a measurement result of scattered X-rays derived from the X-ray imaging device by subtracting an integrated value of signals output from the dosimeter during a period in which the particle beam irradiation is stopped from an integrated value of signals output from the dosimeter; and
determine whether a planned dose has been emitted based on a result of the exclusion.

2. The particle therapy system according to claim 1,
wherein the control apparatus is further configured to:
stop the particle beam irradiation before the X-ray irradiation and to resume the particle beam irradiation upon completion of the X-ray irradiation;
integrate the signals output from the dosimeter;
integrate the signals output from the dosimeter while the particle beam irradiation is being stopped;
subtract an integrated value of a subtraction integration counter from an integrated value of an integration counter; and
determine whether a planned dose has been emitted based on a result of computation by subtracting the integrated value of the subtraction integration counter from the integrated value of the integration counter.

3. The particle therapy system according to claim 2, the particle therapy system dividing the target into a plurality of irradiation regions each constituting a spot and irradiating each spot with the particle beam,
wherein the control apparatus further includes an irradiation controller and an X-ray imaging controller for outputting a signal to the irradiation controller after the X-ray irradiation has ended until before a predetermined time of the X-ray irradiation is resumed; and
wherein, when the signal from the X-ray imaging controller is interrupted, the irradiation controller performs control to stop an update of a current spot position with a next spot position, the current spot position being irradiated with the particle beam while the signal is being received.

4. The particle therapy system according to claim 2,
wherein the control apparatus further includes an irradiation controller and an X-ray imaging controller for outputting a signal to the irradiation controller after the X-ray irradiation has ended until the X-ray irradiation is resumed; and
wherein, when the signal from the X-ray imaging controller is interrupted, the irradiation controller performs control immediately to stop the particle beam irradiation.

5. The particle therapy system according to claim 1,
wherein the control apparatus excludes the measurement result of the scattered X-rays by performing control to separate chronologically a timing of the particle beam irradiation from a timing of an X-ray irradiation performed by the X-ray imaging device.

6. The particle therapy system according to claim 5,
wherein the control apparatus integrates signals from the dosimeter only during a period in which the particle beam is emitted.

7. The particle therapy system according to claim 4,
wherein the irradiation controller has a dose control system that excludes the measurement result of scattered X-rays derived from the X-ray imaging device from a measurement result obtained using the dosimeter.

8. The particle therapy system according to claim 7,
wherein the dose control system includes the integration counter and the subtraction integration counter.

9. The particle therapy system according to claim 3,
wherein the irradiation controller includes a dose control system that excludes the measurement result of scattered X-rays derived from the X-ray imaging device from a measurement result obtained using the dosimeter.

10. The particle therapy system according to claim 9,
wherein the dose control system includes the integration counter and the subtraction integration counter.

11. The particle therapy system according to claim 2,
wherein the control apparatus includes an irradiation controller including a dose control system that excludes the measurement result of scattered X-rays derived from the X-ray imaging device from a measurement result obtained using the dosimeter.

12. The particle therapy system according to claim 11,
wherein the dose control system includes the integration counter and the subtraction integration counter.

13. A particle therapy system comprising:
a particle beam generator for generating a particle beam;
an irradiation nozzle arranged in a treatment room and irradiating a target with the particle beam, the irradiation nozzle having a dosimeter arranged at a position passed by the particle beam;
a particle beam transport system for communicating the particle beam generator with the irradiation nozzle;
an X-ray imaging device arranged in the treatment room and imaging a position of the target through irradiation with X-rays; and
a control apparatus configured to:
exclude a measurement result of scattered X-rays derived from the X-ray imaging device from a measurement result obtained using the dosimeter; and
determine whether a planned dose has been emitted based on a result of the exclusion;

wherein the control apparatus excludes the measurement result of the scattered X-rays by subtracting the measurement result of the scattered X-rays from the measurement result obtained using the dosimeter;

wherein the target is divided into a plurality of irradiation regions each constituting a spot and irradiating each spot with the particle beam;

wherein the control apparatus stops particle beam irradiation before X-ray irradiation performed by the X-ray imaging device and resumes the particle beam irradiation upon completion of the X-ray irradiation by the X-ray imaging device, the control apparatus excluding the measurement result of the scattered X-rays derived from the X-ray imaging device by subtracting from an integrated value of signals output from the dosimeter an integrated value of signals output from the dosimeter during a period in which the particle beam irradiation is stopped;

wherein the control apparatus is further configured to:

stop the particle beam irradiation before the X-ray irradiation and to resume the particle beam irradiation upon completion of the X-ray irradiation;

integrate the signals output from the dosimeter;

integrate the signals output from the dosimeter while the particle beam irradiation is being stopped;

subtract an integrated value of a subtraction integration counter from an integrated value of an integration counter; and determine whether a planned dose has been emitted based on a result of computation by subtracting the integrated value of the subtraction integration counter from the integrated value of the integration counter.

14. The particle therapy system according to claim 13, wherein the control apparatus further includes an irradiation controller and an X-ray imaging controller for outputting a signal to the irradiation controller after the X-ray irradiation has ended until before a predetermined time of the X-ray irradiation is resumed; and wherein, when the signal from the X-ray imaging controller is interrupted, the irradiation controller performs control to stop an update of a current spot position with a next spot position, the current spot position being irradiated with the particle beam while the signal is being received.

15. The particle therapy system according to claim 13, wherein the control apparatus further includes an irradiation controller and an X-ray imaging controller for outputting a signal to the irradiation controller after the X-ray irradiation has ended until the X-ray irradiation is resumed; and wherein, when the signal from the X-ray imaging controller is interrupted, the irradiation controller performs control immediately to stop the particle beam irradiation.

16. The particle therapy system according to claim 15, wherein the irradiation controller has a dose control system that excludes the measurement result of scattered X-rays derived from the X-ray imaging device from the measurement result obtained using the dosimeter.

17. The particle therapy system according to claim 15, wherein the dose control system includes the integration counter and the subtraction integration counter.

18. The particle therapy system according to claim 14, wherein the irradiation controller includes a dose control system that excludes the measurement result of scattered X-rays derived from the X-ray imaging device from the measurement result obtained using the dosimeter.

19. The particle therapy system according to claim 18, wherein the dose control system includes the integration counter and the subtraction integration counter.

20. The particle therapy system according to claim 13, wherein the irradiation controller includes a dose control system that excludes the measurement result of scattered X-rays derived from the X-ray imaging device from the measurement result obtained using the dosimeter.

* * * * *